Figure 1:
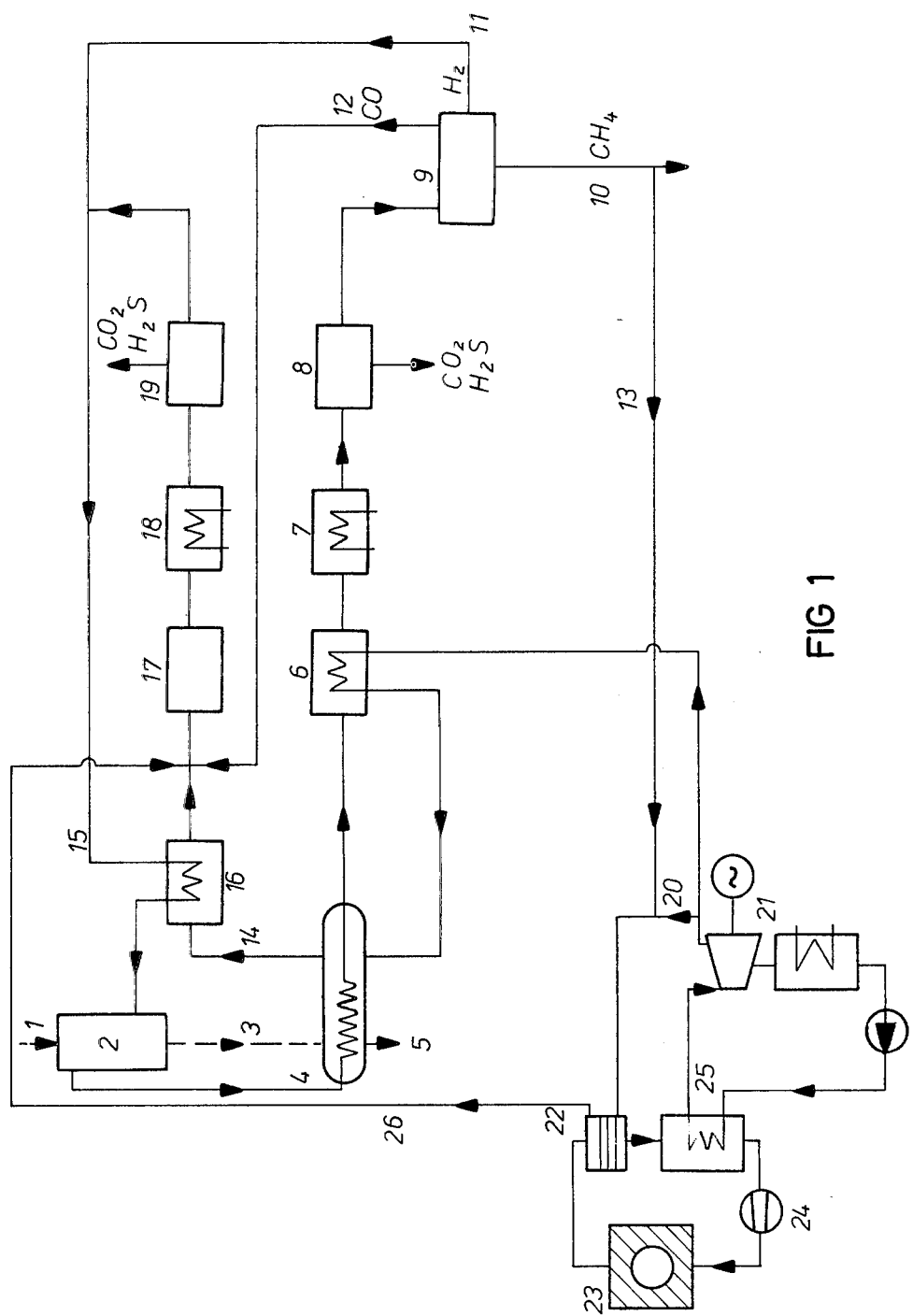

United States Patent [19]

Fischer et al.

[11] 4,328,009
[45] May 4, 1982

[54] COAL GASIFICATION

[75] Inventors: Reimer Fischer, Bergisch Gladbach; Walter Jäger, Engelskirchen; Herbert von Wacławiczek, Bergisch Gladbach, all of Fed. Rep. of Germany

[73] Assignee: GHT Gesellschaft für Hoch-Temperaturreaktor-Technik mbH, Bergisch Gladbach, Fed. Rep. of Germany

[21] Appl. No.: 192,514
[22] PCT Filed: Aug. 21, 1979
[86] PCT No.: PCT/DE79/00093
§ 371 Date: Apr. 29, 1980
§ 102(e) Date: Apr. 29, 1980
[87] PCT Pub. No.: WO80/00442
PCT Pub. Date: Mar. 20, 1980

[30] Foreign Application Priority Data

Aug. 31, 1978 [DE] Fed. Rep. of Germany ....... 2837988

[51] Int. Cl.³ .............................. C10J 3/10; C10J 3/14; C10J 3/18
[52] U.S. Cl. ........................................ 48/202; 48/210; 252/373; 376/325
[58] Field of Search ...................... 48/202, 210, 65, 77, 48/197 R; 252/373; 176/39; 422/199

[56] References Cited

U.S. PATENT DOCUMENTS 1,790,853 2/1931 Casale ................................. 422/199
4,005,045 1/1977 Haese ................................. 176/39
4,095,959 6/1978 Kunstle et al. ..................... 48/77

FOREIGN PATENT DOCUMENTS 1244120 7/1967 Fed. Rep. of Germany .
2553506 6/1977 Fed. Rep. of Germany ........ 48/210
2704465 8/1978 Fed. Rep. of Germany .

OTHER PUBLICATIONS

Chemie-Ing. Techn. 46 Jahrg. 1974/Nr. 22-"Vergasing von Kohle mit Kernreaktorwärme" by Juntgen et al, pp. 937, 938 and 941.
Oak Ridge Nat'l. Lab.-"Assessment of Very High-Temperature Reactors in Process Applications", by Spiewak et al, publ. Nov. 76, p. 82.

Primary Examiner—Peter F. Kratz
Attorney, Agent, or Firm—Herbert L. Lerner; Laurence A. Greenberg

[57] ABSTRACT

Generating methane or synthesis gas from carbon-containing materials, e.g. coal, by reacting part of the carbon with hydrogen in a hydrogenating gasifier to produce a methane containing gas, and reacting the residual carbon with steam in a steam gasifier to produce a raw gas containing synthesis gas, which latter may be converted to hydrogen and directed to the hydrogenation gasifier or may at least in part be used as a product. The steam gasifier is heated with raw gas leaving the hydrogenating gasifier. The hydrogen gas entering the hydrogenation gasifier is heated with the raw gas leaving the steam gasifier. At least part of the methane is reacted with steam to synthesis gas while heat is being supplied.

3 Claims, 2 Drawing Figures

COAL GASIFICATION

The present invention relates to a plant for producing methane or synthesis gas from carbon containing materials, particularly through utilization of nuclear energy. In this process, a first part of the carbon is reacted with hydrogen to methane in a hydrogenating gasifier, and a second part of the carbon is reacted with steam to synthesis gas in a steam gasifier; at least part of the methane is reacted with steam to synthesis gas, heat being supplied. These plants furnish either methane ($CH_4$) or synthesis gas ($H_2$ and $CO$) or both gases at any desired ratio.

Figure 2:
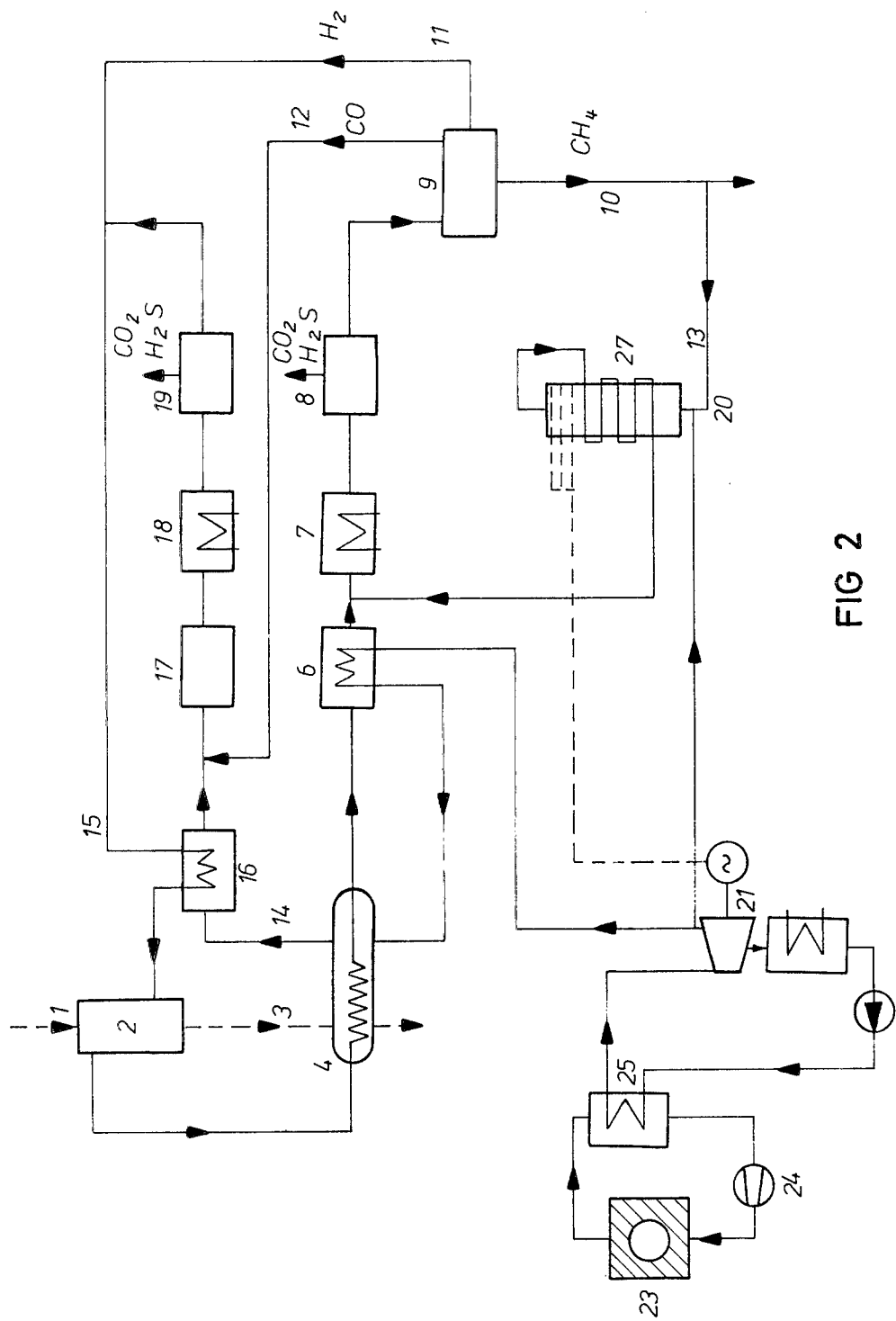

In the journal "Chemie-Ingenieur-Technik" 1974 a process schematic each is described on page 938, particularly in FIG. 1 as well as on page 941, particularly in FIG. 2 for producing methane via steam gasification of coal. On page 937, new processes of a hydrogenating gasification of coal to methane are mentioned. However, both methods have a considerable disadvantage. In the hydrogenating gasification, no complete reaction of the coat is attainable because of the long dwelling times of the coal and with consideration of the limited dimensions of the gasifier. The residual coke obtained in the hydrogenating gasification contains, besides the ash, still also about 30 to 45% of the carbon charged-in. While with steam gasification on the other hand, the charged-in carbon can be gasified nearly without residue, this process, however, takes place only at high temperatures (bituminous coal, 790° C., lignite, 630° to 660° C.) and only the heat released in the reactor in the upper temperature range can be utilized for gasification. The remaining heat can be utilized in a pure steam gasification process substantially only for steam generation and therefore for the generation for electric power, because only a small portion of this steam can be used in the process.

In the report ORNL/TM-5242 (Oak Ridge National Laboratory, Nov. 1976), a plant is shown on page 82 in which carbon is reacted into methane by means of nuclear heat. The coal is first dried, then gasified by hydrogenation and the remaining coke is converted into synthesis gas in a steam gasifier. Part of the methane produced is reacted in a methane cracking furnace (called a reformer there) into synthesis gas, with the addition of hot steam. However, this arrangement still has the following disadvantages: The process heat exchangers which are arranged in a primary but also in a secondary helium loop are very expensive. On the one hand, piping and apparatus carrying helium place more stringent requirements on the tightness, and on the other hand it must be prevented that undesired substances slip into the primary loop in this manner and exert there either a corroding effect, form undesirable deposits or are activated in such a manner that they cause disturbances at other points. Furthermore, all process heat exchangers heated with pure helium have the disadvantage that helium, being a single-atom gas, gives off no radiation heat, which is a disadvantage, particularly at the high temperatures provided here. Therefore, the helium velocity would have to be increased in order to increase the heat transfer by convection, which increases the pressure loss, or the heating surfaces would have to be increased.

In German Published Non-Prosecuted Application No. 25 53 506.2, a plant for producing methane or synthesis gas from carbon-containing materials by means of a nuclear reactor is described wherein part of the carbon-containing material is converted into synthesis gas in a steam gasifier, steam being added, and at high temperature. This plant has two reactor cooling loops; the steam gasifier is arranged in a first cooling loop and in a second cooling loop a cracking furnace (reformer), known per se is arranged in which part of the methane produced is cracked at high temperature to form hydrogen which is used for the hydrogenating gasification of another part of the carbon-containing material. This two-stage gasification combines in an advantageous manner the following requirements: Low coal consumption, complete gasification of the coal, incorporation of almost the entire nuclear reactor heat into the gasification process so that almost no electric power needs to be given off to the outside, and high overall efficiency. A disadvantage is still that for the steam gasifier the necessary heating at high temperature must be made available either directly or via an intermediate loop by the helium which is heated by nuclear energy. This helium would have to have a temperature of about 900° to 950° C. and the portions of the plant between the nuclear reactor and the gasification plant must be suitable for this high temperature. The secondary helium loop which transfers the heat of the nuclear reactor from the primary loop thereof to the gasification plant is connected with considerable cost and also with additional losses. The close coupling between the nuclear reactor plant and the gasification plant necessitates considerable technical means for safety and makes the operation of the overall plant more difficult.

The object of the present invention is a plant for generating methane or synthesis gas from carbon-containing materials which largely avoids the disadvantages described and is largely decoupled from the nuclear reactor plant so that disturbances in the one plant cannot directly effect the other plant. This plant should furthermore not require appreciable amounts of electric power from the outside nor give it off to the outside i.e. it should be self-sufficient.

For solving this problem, a plant is proposed for producing methane or synthesis gas from carbon-containing materials, especially through utilization of nuclear energy; in this process, a first part of the carbon is reacted with hydrogen to methane in a hydrogenating gasifier and a second part of the carbon is reacted with steam to synthesis gas in a steam gasifier, at least part of the methane is reacted with steam to synthesis gas while heat is being supplied. This plant has the following features:

(a) The steam gasifier is heated with the raw gas leaving the hydrogenating gasifier, (b) The hydrogen gas entering the hydrogenation gasifier is heated with the raw gas leaving the steam gasifier. Since the raw gas leaves the hydrogenating gasifier with a very high temperature and since it is uneconomical to utilize this high temperature, as heretofore, only for preheating the entering raw gas or only for generating steam, a high overall efficiency of the plant can be expected with this arrangement. The requirements as to tightness of a heat exchanger particularly in the area of the steam gasifier are considerably less stringent if only process gases are carried on both sides and not a reactor coolant. The dust contained in the raw gas can be separated, for instance, as described in German Pat. No. 12 44 120. The most important advantage of this plant is, however, that the gasification plant is largely decoupled from its energy supply, particularly a nuclear reactor plant. For safety reasons, nuclear power plants are arranged in a so-called containment, which encloses all radioactive loops and which can be closed off completely in the event of an accident. Piping for water or steam or also for gas can pass through this containment. Continuous charging of large amounts of solids and removing the residual coke or ash through locks, however, is connected with considerable expense. In addition, the gasifier can be operated at the most advantageous operating pressure, for instance 80 bar, independently of the reactor.

The plant with the following features:

(a) The methane cracking furnace is heated by a helium-cooled high-temperature reactor, (b) The remaining nuclear reactor heat is given off to a steam loop, has as the only coupling element between the gasification plant and the nuclear reactor, a methane cracking furnace (reformer) which can be arranged inside the containment with a small amount of technical means and can also be heated directly by the reactor cooling helium without a secondary cooling loop. This methane cracking furnace should be preceded in the customary manner by a recuperative heat exchanger which transfers a large part of the heat of the outgoing synthesis gas to the entering methane so that the gas lines passing through the container have only low temperatures and the gasification plant can be placed at a distance from the reactor which is sufficient for safety reasons.

The plant with the following features:

(a) The methane cracking furnace is heated electrically in the upper temperature range, (b) The raw gas leaving the methane cracking furnace serves for heating the entering methane, (c) The entire nuclear reactor heat is given off to a steam loop, has a still farther-reaching separation between the energy supply and gasification plant. If the methane cracking furnace is heated electrically, the nuclear reactor, which may be a high-temperature reactor as well as a pressurized-water reactor, can be separated even more from the gasification plant. As the only lines which must pass through the containment of the nuclear reactor, only water or steam lines are still provided, the technology of which belongs in the meantime to the safe state of the art in the case of nuclear reactor plants. Naturally, the energy transfer from the nuclear reactor via steam generators, turbine and generator down to the electric heating is accompanied by a lower efficiency than with direct heating. Since, however, only part of the nuclear power is utilized for generating electric power and a large part of the nuclear energy is introduced into the gasification plant as process steam without appreciable losses, the overall plant has a tolerable efficiency with substantially lower investment costs. Under these circumstance, the nuclear energy can even be made available, for instance, with a pressurized-water reactor. For prototype or experimental plants or also for smaller gasification plants it may even make sense to make available the energy required for electric power and process steam supply in part by conventional combustion, for instance, of lower grade fuels.

The plant with the following features:

(a) The methane cracking furnace is heated by a helium-cooled high-temperature reactor, (b) The remaining nuclear reactor heat is given off to a steam loop, serves for the production of synthesis gas and therefore has a methane cracking furnace which, however, is heated only electrically, in contrast to the above. Here, a particular operating advantage of electric heating manifests itself over direct heating with helium. The catalyst can be replaced when needed without shutting down the reactor, because in plants of this kind, numerous parallel-connected cracking furnaces are probably available of which always one can be separated from the plant and serviced without interfering with the rest of the plant.

FIG. 1 shows a highly schematized example of the invention. The milled and dried coal is fed at 1 to the hydrogenating gasifier 2 and is gasified there with exothermic hydrogenation. The residual coke obtained there is fed to the steam gasifier 4 via the path 3 and is gasified further. The residue contained there consists of ash with a small amount of carbon and is drawn off at 5. The raw gas leaving the hydrogenating gasifier 2 gives off part of its heat in the upper temperature range in the steam gasifier 4 and in the lower temperature range, in the process steam superheater 6 and the steam generator 7. After it is cooled down and dust and tar have been removed, the raw gas is freed in a gas scrubber 8 or carbon dioxide and hydrogen sulfide. In the low temperature decomposition plant 9, the purified gas is decomposed into a methane fraction 10, into a hydrogen fraction 11 and a carbon monoxide fraction 12. Methane is fed in part to a gas network and in part to a cracking furnace via the pass 13. The hydrogenation gas leaving the steam gasifier 4 via the pass 14 gives off part of its heat to the hydrogenation gas 15 which is to be fed to the hydrogenating gasifier 2 in the heat exchanger 16. The carbon monoxide contained in the hydrogenation gas is converted in the converter 17 with steam into hydrogen and carbon dioxide. Thereupon, the hydrogenation gas is further cooled down in the waste-heat boiler 18, generating process steam. After carbon dioxide and hydrogen sulfide have been removed in the gas scrubber 19, the gas purified in this manner is preheated with the hydrogen given off by the low-temperature decomposition plant 9 via the path 15 in the heat exchanger 16 and is fed to the hydrogenating gasifier 2 where it converts a large part of the carbon into methane. The methane stream 13 leaving the low-temperature gas decomposition 9 is mixed at 20 with steam from the steam power plant 21 and cracked in the helium-heated tube cracking furnace 22 into carbon monoxide and hydrogen with a small amount of methane and steam. The thermal energy required therefore is supplied by a high temperature reactor 23, the closed helium loop of which is operated with a blower 24 and which gives the heat which is not usable in the cracking furnace 22 to a steam generator 25. The hydrogenating gas leaving the cracking furnace 22 has given off a large part of its steam recuperatively to the entering methane and is admixed to the hydrogenating gas leaving the steam gasifier 4, on the way 26 prior to conversion to the converter 17.

FIG. 2 shows a further highly schematized example of the invention. In contrast to the plant already described in FIG. 1, a methane cracking furnace 27 is provided here instead of the helium-heated methane cracking furnace 22; in its upper temperature range, the former is heated with electric current from the steam-turbine plant 21 and is supplied at 20 with a mixture of methane and steam. The cracked (or reformed) raw gas produced serves for heating the entering methane steam mixture in cross-current flow and is fed to the raw gas leaving the steam gasifier between the process steam heater 6 and the process steam generator 7. This plant does not depend on a gas-cooled high temperature reactor and can also be supplied with energy by a light-water reactor via a steam loop. Since a large part of the steam heated by nuclear energy is utilized directly in the plant, the lower thermal efficiency of the light-water reactor is somewhat compensated, especially in smaller plants, by the lower investment costs.

The following numerical examples relate to coal gasification plants which are heated with a high temperature reactor or a light-water reactor.

| | |
|---|---|
| Thermal reactor output: | 1 500 MW |
| Grade of coal: Long-flame gas coal with 38% volatile components | |

EXAMPLE 1

Production of SNG:

| | |
|---|---|
| Coal throughput: | 531 t/h |
| Product: | $381.10^3$ $m_N^3$/h |
| Calorific value: | 40 693 KJ/$m_N^3$ |
| Composition: | 95% $CH_4$ and 5% $C_2H_6$ |

EXAMPLE 2

Production of synthesis gas:

| | |
|---|---|
| Coal throughput: | 433 t/h |
| Product: | 1 249 $m_N^3$/h |
| Calorific value: | 8 673 KJ/$m_N^3$ |
| Composition: | 68% $H_2$ and 32% CO |

We claim:

1. Method for obtaining methane or synthesis gas from carbon-containing material which comprises subjecting a first part of the carbon in the carbon containing material to hydrogenation in a hydrogenation gasifier to react with hydrogen to produce gaseous constituents containing methane which are released from the hydrogenation gasifier, introducing a hydrogen-containing gas into the hydrogenation gasifier, passing the residual part of the carbon in the form of coke from the hydrogenating gasifier into a steam gasifier, introducing steam into the steam gasifier to convert the carbon therein to gases containing synthesis gas which is released from an outlet of the steam gasifier, and heating at least part of the methane obtained from the hydrogenating gasifier in a methane cracking furnace in the presence of steam to effect reaction of methane with steam to produce synthesis gas, the combination therewith of heating the steam gasifier by indirect heat exchange with the gaseous constituents released from the hydrogenation gasifier by passing said gaseous constituents through tubes in a steam gasifier, heating the hydrogen containing gas entering the hydrogenation gasifier by indirect heat exchange with the gases containing synthesis gas released from the steam gasifier and heating the methane entering the methane cracking furnace initially by indirect heat exchange with the raw synthesis gas produced in the methane cracking furnace, and heating the methane in the upper temperature range in the methane cracking furnace via an electrical auxiliary heater connected to a turbo generator, and wherein a steam generator arranged in the cooling circuit of a nuclear reactor supplies steam to operate said turbogenerator and steam for said steam gasifier.

2. Method according to claim 1 wherein the steam generator is arranged in the cooling circuit of a helium cooled high temperature nuclear reactor.

3. Method according to claim 1 wherein the steam generator is the sole coupling between said nuclear reactor and the gasification operation.

* * * * *